United States Patent [19]

Yamada et al.

[11] Patent Number: 5,468,503
[45] Date of Patent: Nov. 21, 1995

[54] ORAL PHARMACEUTICAL PREPARATION RELEASED AT INFRAGASTROINTESTINAL TRACT

[75] Inventors: Akiya Yamada, Takamatsu; Takahiko Wato; Naoki Uchida, both of Kagawa; Misuzu Fujisawa, Takamatsu; Shigeyuki Takama, Kagawa; Yukiko Inamoto, Takamatsu, all of Japan

[73] Assignee: Teikoku Seiyaku Kabushiki Kaisha, Kagawa, Japan

[21] Appl. No.: 78,294

[22] PCT Filed: Aug. 13, 1992

[86] PCT No.: PCT/JP92/01037

§ 371 Date: Jun. 25, 1993

§ 102(e) Date: Jun. 25, 1993

[51] Int. Cl.$^6$ .................................................. A61K 9/62
[52] U.S. Cl. ...................... 424/461; 424/451; 424/457; 424/462
[58] Field of Search ..................... 424/451, 457, 424/458, 461, 462; 74/781, 784, 962, 963

[56] References Cited

U.S. PATENT DOCUMENTS 4,895,724  1/1990  Cardinal et al. ........................ 424/418
5,217,720  6/1993  Sekigawa et al. ...................... 424/480

FOREIGN PATENT DOCUMENTS 3-255037  11/1991  Japan .
4-41422   2/1992   Japan .

OTHER PUBLICATIONS

Miyazakidalin Chemical Pharmaceutical Bulletin vol. 29 No. 10 pp. 3067–3069 (1981).
CA 118 (8): 66904j (1994).
JP 04264022 Abstract Sep. 18, 1992.
Remington's pharmaceutical Sciences, p. 1606 (1985).

*Primary Examiner*—Jyothsna Venkat
*Attorney, Agent, or Firm*—Oblon, Spivak, McClelland, Maier, & Neustadt

[57] ABSTRACT

An oral pharmaceutical preparation of a type released at infragastrointestinal tract was successfully prepared, wherein a solid organic acid dissolvable, in the form of a solution, of chitosan and a solid pharmaceutical preparation including a principal agent are filled in a hard capsule composed of the base principally comprising chitosan and an enteric coating is formed on the surface of the hard capsule, characterized in that a desirable releasing time can be arranged, with no pH dependency, via water permeability derived from the porosity of chitosan of the capsule preparation.

5 Claims, 2 Drawing Sheets

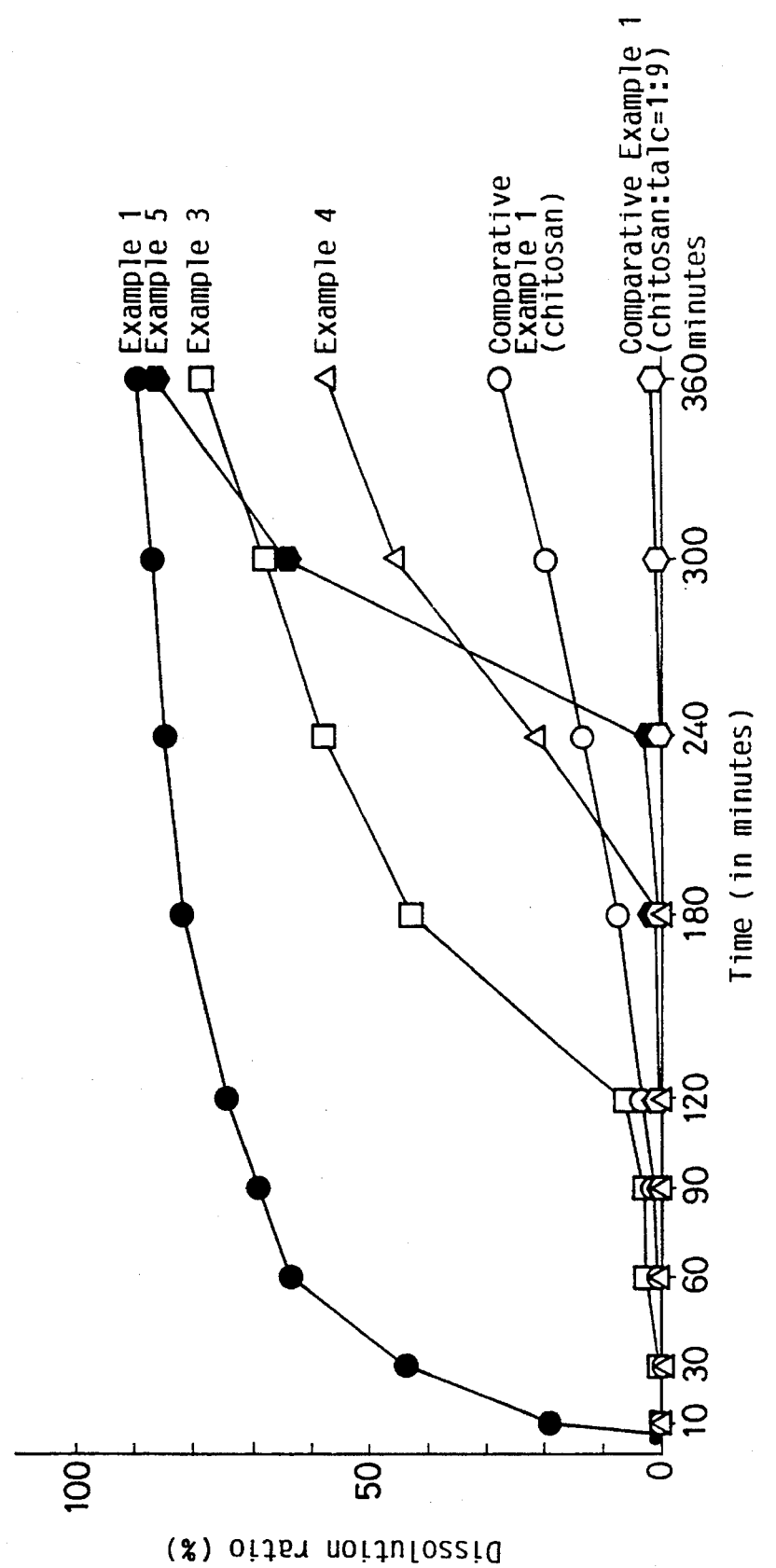

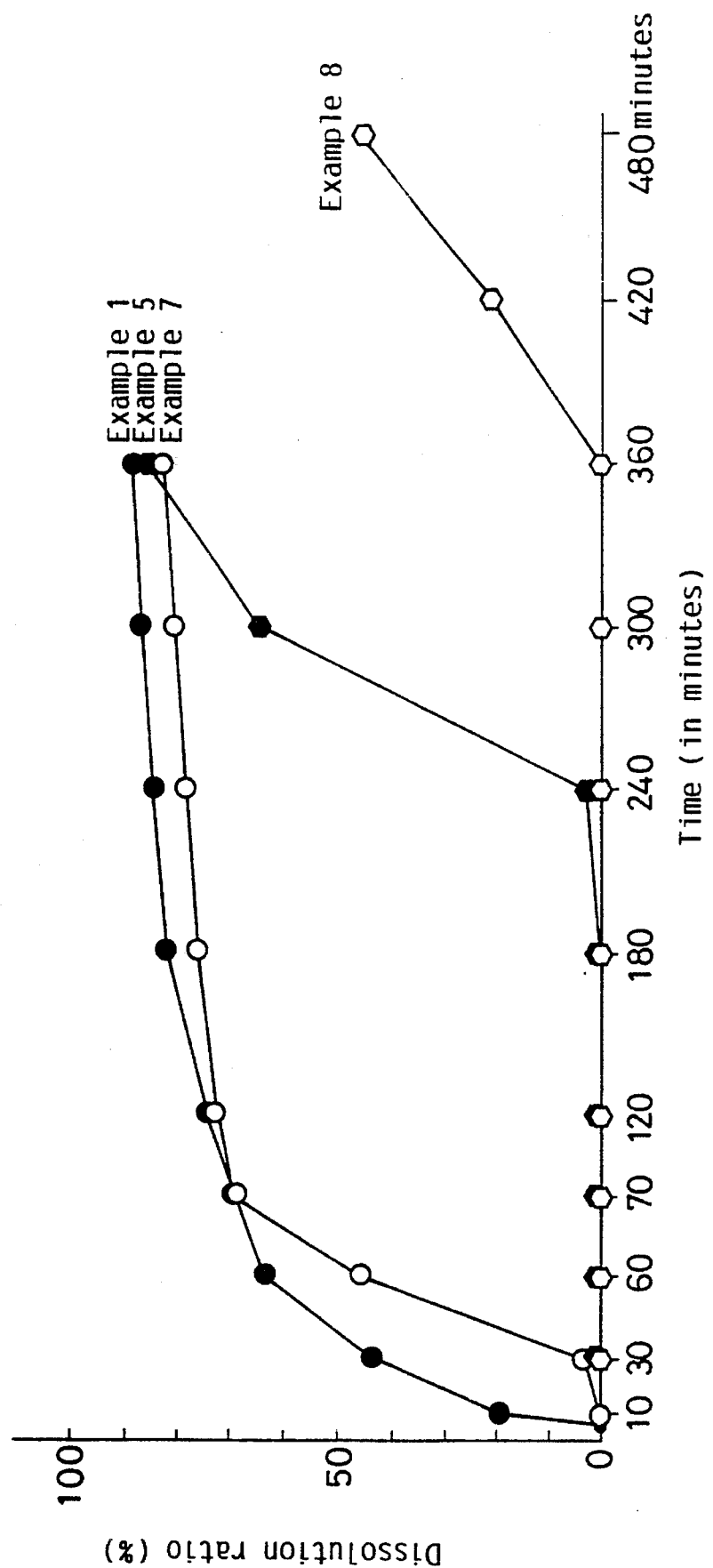

ORAL PHARMACEUTICAL PREPARATION RELEASED AT INFRAGASTROINTESTINAL TRACT

TECHNICAL FIELD

The present invention relates to an oral pharmaceutical preparation of a type released at infragastrointestinal tract for releasing a principal agent having pharmacological actions at infragastrointestinal tract after the oral dosage thereof.

BACKGROUND OF THE INVENTION

Chitin is contained in the exoskeleton of crustaceans such as crab, shrimp, krill, etc. and insects, as the constituent components thereof, and is a naturally occurring basic polysaccharide present in nature in widespread manner. The chitin having a linear chain bonded with N-acetyl-D-glucosamine and chitosan produced through the deacetylation of chitin have been neglected and left alone as unused biological resources for a long period of time. In recent years, however, the absence of toxicity and the physico-chemical properties have been drawing attention, leading to the progress in the active research works for effective application of chitin and chitosan. Thus, expectation has been directed toward the application thereof in a wide variety of fields, for example, as coagulants, ion exchangers, enzyme immobilizing agents, raw materials for hair cosmetics, medicinal materials, food additives, soil modifiers, etc. Chitosan, in particular, is promising because it has advantages, for example, in that it is readily dissolved in dilute hydrochloric acid, aqueous solutions of organic acids and the like, and that the glucosamine residue constituting the molecular chain is a high molecular electrolyte having a free primary amine group ($-NH_2$).

In the field of pharmaceutical products, alternatively, investigation has been carried out toward a preparation technique for advancing a pharmaceutical preparation to infragastrointestinal tract such as the lower part of small intestine, large intestine, etc., while suppressing the release of the preparation in stomach and the upper part of small intestine after the oral dosage thereof.

Because physiologically active polypeptide hormones such as insulin and calcitonin are water-soluble, high molecular compounds readily decomposed via intestinal proteases such as gastric juice, pepsin and trypsin, the development of an oral pharmaceutical preparation of a type released at infragastrointestinal tract is significant so as to make the polypeptide hormones absorbed at infragastrointestinal tract without the decomposition via the aforementioned proteases. The development is also significant from the respect that pharmaceutical agents effective for diseases of infragastrointestinal tract, such as ulcerative colitis and Chron's disease, be administered directly to the lesions without the occurrence of side effects.

The aforementioned various pharmaceutical agents in the form of parenteral administration have been developed, but they have drawbacks in not only practical inconvenience of complex procedures but also heavy burdens to patients. From such standpoint, the agents are desirably in the form of oral administration as possible.

In conventional oral pharmaceutical preparations of a type released at infragastrointestinal tract, generally, the surface thereof is film coated with a polymer compound dissolvable at a higher pH, and the resulting thickness serves to adjust the absorption site thereof. However, problems have been suggested in that the pH level in gastrointestinal tract varies depending on individuals and that the variation in the site where such pH-dependent preparations as those described above are degraded readily occurs, depending on individuals. If such preparations are degraded, for example, at the upper part of small intestine to release the pharmaceutical agents thereof, some of the agents (for example, the aforementioned polypeptides and the like) may be decomposed without exhibiting the drug efficacy. If the pH value in large intestine is declined because of the metabolism via intestinal bacteria or the like, the coating film provided for the preparations is not dissolved, resulting in no release of the pharmaceutical agents and no exhibition of pharmacological actions. Hence, the preparations are excreted as they are. Proposition has been made of a technique comprising using a polymer film degradable via the bacteria in large intestine and degrading a pharmaceutical preparation in large intestine, but the technique has problems in that such pharmaceutical preparation also causes the variation in the degradation time, depending on the individual difference in the bacteria in large intestine and that the degradation of the polymer film requires a long period of time.

The present invention has been achieved in such circumstances. It is an object of the present invention to provide an optimum form of an oral pharmaceutical preparation of a type released at infragastrointestinal tract by effectively utilizing chitosan.

DISCLOSURE OF THE INVENTION

The present invention which has achieved the aforementioned objective is summarized in an oral pharmaceutical preparation of a type released at infragastrointestinal tract for releasing a principal agent therein wherein a solid organic acid dissolvable, in the form of a solution, of chitosan and a solid pharmaceutical preparation including the principal agent are filled in a hard capsule composed of the base principally comprising chitosan and anenteric coating is formed on the surface of the hard capsule. In the above constitution, the permeability of water into the capsule is adjusted through the thickness of the hard capsule and the physico-chemical properties of chitosan, thereby regulating, with no pH dependency, the site where the pharmaceutical agent (principal agent) is released. Alternatively, a lubricating agent is effectively contained in a capsule base, and the regulation of the releasing site is also possible through the adjustment of the ratio of chitosan to a lubricating agent in the base.

BRIEF DESCRIPTION OF THE INVENTION

FIG. 1 shows graphs depicting the results of the dissolution test of Example 11; and FIG. 2 shows graphs depicting the results of the dissolution test of Example 12.

BEST MODE FOR CARRYING OUT THE INVENTION

Based on the standpoint that non-toxic chitosan should effectively be utilized as a raw material of an oral pharmaceutical preparation of a type released at infragastrointestinal tract, the present inventors have made investigations about such pharmaceutical preparation in the optimum form from various respects. Consequently, the present inventors have found that the above objective can satisfactorily be achieved if employing a constitution such that a solid organic acid dissolvable, in the form of a solution, of chitosan and a solid pharmaceutical preparation including a principal agent are filled in a hard capsule principally comprising chitosan and an enteric coating is formed on the surface of the hard capsule. Thus, the present invention has been achieved.

The releasing mechanism of the principal agent of the pharmaceutical preparation of the present invention is as follows. The orally administered pharmaceutical preparation of the present invention reaches stomach to the upper part of small intestine, while the degradation thereof is prevented via the enteric coating at the most exterior layer. The enteric coating is dissolved in the upper part of small intestine. Thereafter, water gradually permeating into the hard capsule principally comprising chitosan dissolves the solid organic acid in the capsule into an aqueous solution. The aqueous solution of the organic acid dissolves chitosan, a composition of the hard capsule, and gradually degrades the hard capsule, involving the release of the principal agent inside the capsule. The constitution utilizing the water permeation into the hard capsule in such manner with no pH dependency should be employed with no occurrence of disadvantages as those described about the prior art.

In accordance with the present invention, the time period required for water permeation into the inside of the capsule after the dissolution and removal of the enteric coating on the surface of the hard capsule can be adjusted through the physico-chemical properties of chitosan (the deacetylation degree, molecular weight and the like) and the capsule thickness. As has been described above, a lubricating agent is effectively contained in the capsule base, while the water permeability into the capsule can be adjusted also through the compounding ratio of chitosan to a lubricating agent, which indicates that the principal agent-releasing site can be regulated appropriately through the physico-chemical properties of chitosan, the capsule thickness, the addition amount of a lubricating agent, and the like.

The chitosan to be used in accordance with the present invention is the one produced by the deacetylation of chitin dissoluble in dilute hydrochloric acid, with no limitation to the origin organisms, purification methods and deacetylation methods of chitin, provided that the deacetylation degree is above 60%. The solvent for dissolving chitosan in producing the hard capsule includes acetic acid, lactic acid, citric acid, malic acid, tartaric acid and the like.

A lubricating agent may be added to the hard capsule if necessary, and illustratively includes talc, magnesium stearate, aluminum stearate (including all of mono-, di- and tristearate), calcium stearate, and the like, and one or more can be used among them. If a lubricating agent is contained therein, a far greater ratio of a lubricating agent renders the hard capsule fragile, disadvantageously involving the occurrence of cracks and the like. The upper limit of the compounding ratio of chitosan to a lubricating agent should be up to about 5:95.

An enteric coating is formed on the surface of the hard capsule. That is, by forming the coating on the surface of the hard capsule, the hard capsule can pass through stomach while the degradation thereof is prevented. The enteric compound as the raw material of such coating includes, for example, methacrylate copolymer (Eudragit L and Eudragit S; all as product names), hydroxypropyl methyl cellulose phthalate (HPMCP), hydroxypropyl methyl cellulose acetate succinate (HPMCAS), cellulose acetate phthalate (CAP), hydroxypropyl methyl cellulose (HPMC), shellac and the like.

If necessary, plasticizers and lubricating agents as those described above may be contained in the coating. The plasticizers include castor oil, polyethylene glycol, sodium citrate, triacetin, the glycerin ester of fatty acids and the like. The pharmaceutical preparation of the present invention is intended for regulating the release site through the thickness of a base of the hard capsule, the physico-chemical properties of chitosan, the addition amount and ratio of a lubricating agent. Hence, the aforementioned enteric coating which dissolution rate is readily exposed to the influence of pH value should be limited to minimum as possible so as to pass the present preparation through stomach.

The solid organic acid to be used in the present invention is in a solid form at room temperature, but in the form of a solution thereof, it dissolves chitosan. As such organic acid, there are illustrated citric acid, tartaric acid, malic acid, succinic acid, adipic acid, benzoic acid and the like, and one or more may be used among them, satisfactorily. The addition amount of such solid organic acid is appropriately at about 5 to 90% to the total amount of the solid pharmaceutical preparation to be filled in the hard capsule, preferably at 10% or more to the amount of chitosan contained in the hard capsule.

The principal agent to be used in the present invention includes, without limitation, a variety of agents as follows; pharmaceutical agents effective for infragastrointestinal tract disorders such as Chron's disease, ulcerative colitis, and colon cancer, including for example, salazosulfapyridine, cortisone acetate, triamcinolone, tegafur, fluorouracil and the like. Also, a variety of polypeptides and the derivatives thereof, which are readily degraded in supragastrointestinal tract and absorbed at infragastrointestinal tract to exhibit physiological activity, may effectively be usable as the principal agents of the present invention, including insulin, calcitonin, angiotensin, vasopressin, desmopressin, leutenizing hormone-releasing hormone (LHRH), somatostatin, glucagon, oxytocin, gastorin, cyclosporin and the like.

The pharmaceutical form of the principal agent to be filled in the capsule includes a variety of forms such as granules, fine granules, powders or tablets, and any of them should be of a solid type containing the solid organic acid described above. In preparing the principal agent into a variety of pharmaceutical preparations, binders, excipients, degrading agents, or lubricating agents as those described above may be usable. Such binders include gelatin, hydroxypropyl cellulose, polyvinylpyrrolidone, and the like. Such excipients include those routinely employed for oral pharmaceutical preparations such as lactose, corn starch, potato starch, crystalline cellulose, and the like. The degrading agent includes calcium carboxymethyl cellulose, hydroxypropyl methyl cellulose at low substitution, and the like.

The oral pharmaceutical preparation of a type released at infragastrointestinal tract in accordance with the present invention can be produced, for example, as follows. A capsule mold is immersed in a chitosan solution or in a lubricating agent-containing chitosan solution, followed by drawing out the mold and subsequent drying; otherwise, the mold is immersed in an appropriate alkali solution in order to remove the acid if necessary, followed by drying, and the dried product is then drawn out from the mold and cut out into a predetermined length to form a hard capsule. In the hard capsule are filled a solid organic acid and a solid pharmaceutical preparation including a principal agent, and the capsule connecting part is bonded with a chitosan solution, an adhesive or the like, followed by drying, thereby coating the enteric coating on the surface of the capsule to produce the pharmaceutical preparation of the present invention.

The pharmaceutical preparation thus obtained, if orally administered, passes through stomach through the action of the enteric coating. Subsequently, water permeates into the capsule via the water permeability derived from the porosity of chitosan and dissolves the solid organic acid inside the capsule into the form of a solution, which then dissolves chitosan as a capsule base, involving the release of the principal agent following the degradation of the preparation at a desirable site of infragastrointestinal tract, to exhibit the pharmacological action, depending on the type of the principal agent.

The present invention will now be explained in details with reference to examples, but is not limited by the following examples. It is to be understood that the modification and variation thereof may be made without departing the spirit and scope of the present invention, described above and below.

EXAMPLE 1

From a chitosan solution prepared so as to get the composition as shown in Table 1, a hard capsule of a thickness of 150 μm was produced by means of a capsule mold composed of a capsule body of 6-mm diameter and a capsule cap of 6.2-mm diameter.

TABLE 1

| Capsule composition | Compounding ratio (g) |
| --- | --- |
| Chitosan | 10 |
| Acetic acid | 5 |
| Distilled water | 55 |

Then, fine granules were prepared by using lactose, corn starch, hydroxypropyl cellulose and triamcinolone as the principal agent among the compositions of the solid pharmaceutical preparation shown in Table 2. Ten grams of citric acid were added to and homogeneously mixed with 10.6 g of the fine, granules, to produce a final fine granule preparation as the solid pharmaceutical preparation.

TABLE 2

| Composition of solid pharmaceutical preparation | Compounding ratio (g) |
| --- | --- |
| Lactose | 6 |
| Cornstarch | 4 |
| Hydroxypropyl cellulose | 0.2 |
| Triamcinolone | 0.4 |
| Citric acid | 10 |

Two hundreds to three hundred milligrams of the fine granule preparation (solid pharmaceutical preparation) were filled in the hard capsule, followed by coating of a chitosan solution on the capsule connecting pad and subsequent drying, to produce an encapsulated pharmaceutical preparation.

EXAMPLE 2

Using the hard capsule shown in Example 1 and the solid pharmaceutical preparation of the composition shown in Table 3, an encapsulated pharmaceutical preparation was produced following the same manner as in Example 1.

TABLE 3

| Composition of solid pharmaceutical preparation | Compounding ratio (g) |
| --- | --- |
| Lactose | 6 |
| Cornstarch | 4 |
| Hydroxypropyl cellulose | 0.2 |
| Fluorouracil | 0.4 |
| Tartaric acid | 10 |

EXAMPLE 3

After preparing a chitosan solution by using chitosan, acetic acid and distilled water, talc was charged and uniformly dispersed in the solution to produce a chitosan-talc kneaded product. From the product, a hard capsule of the composition shown in Table 4 was prepared in the same manner as in Example 1.

TABLE 4

| Capsule composition | Compounding ratio (g) |
| --- | --- |
| Chitosan | 10 |
| Talc | 10 |
| Acetic acid | 5 |
| Distilled water | 75 |

In the hard capsule described above was filled the fine granule preparation prepared in the same fashion as in Table 2 except that the principal agent, cortisone acetate was 10 mg per capsule, followed by coating of the chitosan-talc kneaded product on the capsule connecting part and drying, to produce an encapsulated pharmaceutical preparation.

EXAMPLE 4

Following the same procedures as in Example 3, the hard capsule of the composition of Table 5 was produced. Following the same procedures as in Example 3 except that the principal agent, fluorouracil, was 20 mg in the hard capsule, an encapsulated pharmaceutical preparation was prepared.

TABLE 5

| Capsule composition | Compounding ratio (g) |
| --- | --- |
| Chitosan | 9 |
| Talc | 21 |
| Acetic acid | 4.5 |
| Distilled water | 65.5 |

EXAMPLE 5

Following the same manner as in Example 3, the hard capsule of the composition shown in Table 6 was produced. Following the same procedures as in Example 3 except that the principal agent, insulin, was 10 units in the hard capsule, an encapsulated pharmaceutical preparation was prepared.

TABLE 6

| Capsule composition | Compounding ratio (g) |
| --- | --- |
| Chitosan | 2 |
| Talc | 18 |
| Acetic acid | 1 |
| Distilled water | 19 |

EXAMPLE 6

A chitosan-magnesium stearate kneaded product of the composition shown in Table 7 was produced, from which was subsequently produced a hard capsule following the same procedures as in Example 1.

TABLE 7

| Capsule composition | Compounding ratio (g) |
| --- | --- |
| Chitosan | 10 |
| Magnesium stearate | 10 |
| Acetic acid | 5 |
| Distilled water | 75 |

In the hard capsule described above was filled the fine granule preparation prepared in the same fashion as in Table 2 except that the principal agent, calcitonin, was 20 IU per capsule, followed by coating of the chitosan-magnesium stearate kneaded product on the capsule connecting part and drying, to produce an oral pharmaceutical preparation of a type released at infragastrointestinal tract.

EXAMPLE 7

Following the same procedures as in Example 1, using a chitosan solution of the composition shown in Table 1, except for preparing the thickness at 300 μm, a hard capsule was prepared. The solid pharmaceutical preparation shown in Table 2 was filled in the hard capsule following the same manner as in Example 1, to prepare an oral pharmaceutical preparation of a type released at infragastrointestinal tract in accordance with the present invention.

EXAMPLE 8

Following the same procedures as in Example 1 except for using a chitosan-talc kneaded product of the composition shown in Table 6 and preparing the thickness at 300 μm, a hard capsule was prepared. Subsequently, the same procedures as in Example 3 were followed to prepare a hard capsule.

EXAMPLE 9

There were prepared oral pharmaceutical preparations of a type released at infragastrointestinal tract in accordance with the present invention, by using the encapsulated pharmaceutical preparations of Examples 1, 5, 7 and 8, effecting film coating thereon with a coating solution of the composition of Table 8 by means of high coaters, thereby forming enteric coating of a film thickness of 50 μm.

TABLE 8

| Composition of enteric coating | Compounding ratio (g) |
| --- | --- |
| Methacrylate copolymer L (Methacrylic Acid-Methyl Methacrylate Copolymer) | 50 |
| Castor oil | 10 |
| Ethanol | 340 |

Comparative Example 1

Hard capsules of the compositions individually shown in Tables 1 and 6 were prepared. Then, the fine granules of the composition shown in Table 9 were filled in the individual capsules to prepare encapsulated pharmaceutical preparations.

TABLE 9

| Composition of solid pharmaceutical preparations | Compounding ratio (g) |
| --- | --- |
| Lactose | 60 |
| Corn starch | 40 |
| Hydroxypropyl cellulose | 2 |
| Food Red 106 (Acid Red) | 1 |

Comparative Example 2

Following the same manner as in Example 9, enteric coating (film thickness of 50 μm) was formed on the encapsulated pharmaceutical preparations, produced in Comparative Example 1, to prepare oral pharmaceutical preparations of a type released at infragastrointestinal tract.

EXAMPLE 10

According to the 11-th revised edition of Japanese Pharmacopoeia, degradation test was carried out of the encapsulated pharmaceutical preparations, which were obtained in Example 9 and Comparative Example 2 and wherein the principal agents were replaced with Food Red 106 (Acid Red). The test was continued in the first solution of the Degradation Test for 2 hours, and then continued in the second solution thereof for 4 hours at longest. The results in the first solution are shown in Table 10. The results in the second solution are shown in Table 11.

TABLE 10

| Capsule composition | Example 9 | | Comparative Example 2 | |
| --- | --- | --- | --- | --- |
| | Chitosan | Chitosan:Talc = 1:9 | Chitosan | Chitosan:Talc = 1:9 |
| Film thickness | 150 μm | 150 μm | 150 μm | 150 μm |
| Presence of organic acid in solid pharmaceutical preparation contents | Yes (citric acid) | Yes (citric acid) | No | No |
| Period of time required for the initiation of the dissolution of dye contents (on average) | No dissolution | No dissolution | No dissolution | No dissolution |
| Period of time required for the completion of the whole contents' release (on average) | No release | No release | No release | No release |

Note
The contents were absolutely protected with the enteric coating, with no change in the pharmaceutical preparations prior to or after the test.

TABLE 11

| | Example 9 | | Comparative Example 2 | |
|---|---|---|---|---|
| Period of time required for the dissolution and removal of enteric coating (on average) | 5–15 minutes (8.9 minutes) | 5–17 minutes (9.6 minutes) | 4–11 minutes (8.3 minutes) | 5–13 minutes (7.5 minutes) |
| Period of time required for the initiation of the dissolution of dye contents (on average) | 13–20 minutes (17.8 minutes) | 40–65 minutes (57.2 minutes) | 17–28 minutes (25.1 minutes) | 56–89 minutes (69.6 minutes) |
| Period of time required for the completion of the whole contents' release (on average) | 33–51 minutes (46.0 minutes) | 94–148 minutes (121.5 minutes) | 4 hours or more | 4 hours or more |
| Note | An aperture was made on some parts of the capsule, and the whole contents were dissolved or fallen out within 1 hour. | The capsule was opened or degraded, and the whole contents were dissolved or fallen out. | The dye was dissolved, but no degradation of the capsule was observed in 4 hours. | same as left |

EXAMPLE 11

According to the 11-th revised edition of Japanese Pharmacopoeia, Dissolution Test No.1, dissolution test was carried out of the encapsulated pharmaceutical preparations, obtained in Examples 1, 3, 4 and 5 and Comparative Example 1, wherein the pharmacologically active ingredients were replaced with Food Red 106. The Degradation Test No.2 Solution was employed as the testing solution, and the absorbance at a wave length of 565 nm was measured to determine the amount of the dye dissolved from the capsules. Then, the dissolution ratio of the dissolved dye to the dye initially filled in the capsule was determined. The results are shown in FIG. 1.

EXAMPLE 12

Following the same fashion as in Example 11, dissolution test was carried out of the encapsulated pharmaceutical preparations obtained in Examples 7 and 8, wherein the pharmacologically active ingredients were replaced with Food Red 106 (Acid Red). The results are shown in FIG. 2.

INDUSTRIAL APPLICABILITY OF THE INVENTION

The pharmaceutical preparation of a type released at infragastrointestinal tract in accordance with the present invention is a preparation intended for the release of the contents in a shorter time by adjusting the thickness of a capsule principally comprising chitosan, controlling the water permeability derived from the porosity of chitosan, namely, adjusting the infiltration time of water into the capsule, thereby rapidly degrading the capsule at a time when water infiltrates into the inside of the capsule. Thus, the present preparation is effective specifically for the administration of pharmaceutical agents into infragastrointestinal tract, namely, the lower part of small intestine and colon. The present invention can be regarded as an oral pharmaceutical preparation of a releasing type under timing regulation, because the mechanism of advancing the preparation to a site intended for the dosing of the agents is not of the conventional pH-dependent type, but depends on the period of time after the initiation of the contact of chitosin in the hard capsule to water. The pharmaceutical preparation of the present invention, if employed, enables the administration of a pharmaceutical agent whose higher level is required topically for absorption at infragastrointestinal tract. Besides, the preparation brings about effects such that a pharmaceutical agent having local action in infragastrointestinal diseases can be administered to such lesions with efficiency.

What is claimed is:

1. An oral pharmaceutical preparation for releasing a principal agent in the infragastrointestinal tract, comprising:

(a) a hard capsule comprising chitosan and a lubricating agent selected from the group consisting of talc, magnesium stearate, aluminum stearate and calcium stearate;

(b) a solid pharmaceutical preparation comprising said principal agent and a solid water-soluble organic acid which is one or more acids selected from the group consisting of citric acid, tartaric acid, malic acid, succinic acid, adipic acid and benzoic acid; and, (c) an enteric coating comprising one or more polymers selected from the group consisting of hydroxypropyl methyl cellulose phthalate, hydroxypropyl methyl cellulose acetate succinate, cellulose acetate phthalate, methacrylate copolymer and shellac;

wherein said solid pharmaceutical preparation (b) is filled in said hard capsule (a) and said enteric coating (c) is formed on the surface of said hard capsule (a).

2. An oral pharmaceutical preparation according to claim 1, wherein said solid water-soluble organic acid dissolves when contacted with water to form an aqueous solution which is capable of dissolving said chitosan.

3. An oral pharmaceutical preparation for releasing a principal agent in the infragastrointestinal tract, consisting essentially of:

(a) a hard capsule comprising chitosan and a lubricating agent selected from the group consisting of talc, magnesium stearate, aluminum stearate and calcium stearate;

(b) a solid pharmaceutical preparation comprising said principal agent and a solid water-soluble organic acid which is one or more acids selected from the group consisting of citric acid, tartaric acid, malic acid, succinic acid, adipic acid and benzoic acid; and, (d) an enteric coating;

wherein said solid pharmaceutical preparation (b) is filled in said hard capsule (a) and said enteric coating (c) is formed on the surface of said hard capsule (a).

4. The oral pharmaceutical preparation according to claim 3, wherein said enteric coating comprises one or more polymers selected from the group consisting of hydroxypropyl methyl cellulose phthalate, hydroxypropyl methyl cellulose acetate succinate, cellulose acetate phthalate, methacrylate copolymer and shellac.

5. The oral pharmaceutical preparation according to claim 3, wherein said solid water-soluble organic acid dissolves when contacted with water to form an aqueous solution which is capable of dissolving said chitosan.

* * * * *